(12) United States Patent
Chou et al.

(10) Patent No.: US 12,350,305 B2
(45) Date of Patent: Jul. 8, 2025

(54) ACTIVE ESSENCE COMPOUNDED WITH POSTBIOTICS AND PREPARATION METHOD

(71) Applicant: BIO-RACE BIOTECH HANGZHOU CO., LTD., Zhejiang (CN)

(72) Inventors: Dingli Chou, Taichung (CN); Yong Zhang, Anqing (CN)

(73) Assignee: BIO-RACE BIOTECH HANGZHOU CO., LTD., Hangzhou (CN)

( * ) Notice: Subject to any disclaimer, the term of this patent is extended or adjusted under 35 U.S.C. 154(b) by 862 days.

(21) Appl. No.: 17/624,319

(22) PCT Filed: Nov. 3, 2020

(86) PCT No.: PCT/CN2020/126073
§ 371 (c)(1),
(2) Date: Dec. 31, 2021

(87) PCT Pub. No.: WO2021/093632
PCT Pub. Date: May 20, 2021

(65) Prior Publication Data
US 2022/0354913 A1    Nov. 10, 2022

(30) Foreign Application Priority Data

Nov. 15, 2019   (CN) .......................... 201911120976.1

(51) Int. Cl.
| | | |
|---|---|---|
| *A61K 36/185* | (2006.01) | |
| *A61K 8/19* | (2006.01) | |
| *A61K 8/37* | (2006.01) | |
| *A61K 8/44* | (2006.01) | |
| *A61K 8/49* | (2006.01) | |
| *A61K 8/73* | (2006.01) | |
| *A61K 8/9728* | (2017.01) | |
| *A61K 8/9789* | (2017.01) | |
| *A61K 8/9794* | (2017.01) | |
| *A61K 8/99* | (2017.01) | |
| *A61K 31/198* | (2006.01) | |
| *A61K 31/232* | (2006.01) | |
| *A61K 31/4015* | (2006.01) | |
| *A61K 31/715* | (2006.01) | |
| *A61K 33/38* | (2006.01) | |
| *A61K 35/74* | (2015.01) | |
| *A61K 35/741* | (2015.01) | |
| *A61K 35/745* | (2015.01) | |
| *A61K 35/747* | (2015.01) | |
| *A61K 36/06* | (2006.01) | |
| *A61K 36/23* | (2006.01) | |
| *A61K 36/48* | (2006.01) | |

(Continued)

(52) U.S. Cl.
CPC .............. *A61K 36/185* (2013.01); *A61K 8/19* (2013.01); *A61K 8/375* (2013.01); *A61K 8/44* (2013.01); *A61K 8/4913* (2013.01); *A61K 8/73* (2013.01); *A61K 8/735* (2013.01); *A61K 8/9728* (2017.08); *A61K 8/9789* (2017.08); *A61K 8/9794* (2017.08); *A61K 8/99* (2013.01); *A61K 31/198* (2013.01); *A61K 31/232* (2013.01); *A61K 31/4015* (2013.01); *A61K 31/715* (2013.01); *A61K 33/38* (2013.01); *A61K 35/74* (2013.01); *A61K 35/741* (2013.01); *A61K 35/745* (2013.01); *A61K 35/747* (2013.01); *A61K 36/06* (2013.01); *A61K 36/23* (2013.01); *A61K 36/48* (2013.01); *A61K 36/899* (2013.01); *A61K 47/36* (2013.01); *A61Q 19/007* (2013.01); *A61K 2236/15* (2013.01); *A61K 2800/85* (2013.01); *A61K 2800/87* (2013.01)

(58) Field of Classification Search
CPC ............ A61K 2236/15; A61K 2800/85; A61K 31/198; A61K 33/38; A61K 8/73; A61Q 19/007; A61Q 19/00
See application file for complete search history.

(56) References Cited

FOREIGN PATENT DOCUMENTS

| CN | 101962385 | 2/2011 |
|---|---|---|
| CN | 104490748 | 4/2015 |

(Continued)

OTHER PUBLICATIONS

Machine Translation of CN104586737A (Year: 2015).*
Machine Translation of CN107184623 A (Year: 2017).*
Machine Translation of CN108338965A (Year: 2018).*

*Primary Examiner* — Jeffrey T. Palenik
*Assistant Examiner* — Cynthia Ladonna Figgers
(74) *Attorney, Agent, or Firm* — Jiwen Chen; Joywin IP Law PLLC

(57) ABSTRACT

The present invention relates to a multi-postbiotics-compounded rejuvenating essence, which includes the following components in percentage by weight: 8.0-13.0% of butanediol, 2.0-3.0% of triglyceride octoate/caprate/succinate, 2.0-3.0% of polyglutamate sodium, 0.5-1.0% of extract of Japanese *Ardisia* herb stems, 0.5-1.0% of yeast/rice ferment filtrate, 0.5-1.0% of fission yeast mycelium ferment filtrate, 0.5-1.0% of *lactobacillus*/mung bean extract/sodium glutamate ferment filtrate, 0.5-1.0% of *lactobacillus* ferment, 0.5-1.0% of *bacillus*/rice bran extract/soybean extract ferment filtrate, 0.5-1.0% of *Streptococcus thermophilus* ferment, 0.1-0.2% of collargol, and 65.3-79.4% of deionized water, wherein the essence is put in an airtight container and is injected with hydrogen. The present invention can achieve an effect of repairing the skin, and the combination of active substances with the hydrogen injected has a prominent effect on reducing the amount of allergic erythema and alleviating the recurrent allergic redness and rashes.

9 Claims, No Drawings

(51) Int. Cl.
*A61K 36/899* (2006.01)
*A61K 47/36* (2006.01)
*A61Q 19/00* (2006.01)

(56) References Cited

FOREIGN PATENT DOCUMENTS

| | | |
|---|---|---|
| CN | 104586737 | 5/2015 |
| CN | 107184623 | 9/2017 |
| CN | 108338965 | 7/2018 |

\* cited by examiner

ACTIVE ESSENCE COMPOUNDED WITH POSTBIOTICS AND PREPARATION METHOD

This is a U.S. national stage application of PCT Application No. PCT/CN2020/126073 under 35 U.S.C. 371, filed Nov. 3, 2020 in Chinese, claiming priority to Chinese Patent Applications No. 201911120976.1, filed Nov. 15, 2019, all of which are hereby incorporated by reference.

BACKGROUND OF THE INVENTION

1. Technical Field

The present invention belongs to the technical field of skin-care products, and in particular, relates to a multi-postbiotics-compounded rejuvenating essence and a method for preparing the same.

2. Description of Related Art

In recent years, a large number of studies have found that postbiotics have similar effects to probiotics. At present, postbiotics are mainly sourced from the fermentation products of metabolites of *Lactobacillus* and *Bifidobacterium*. The use of postbiotics avoids the problems of probiotics such as low bioavailability and unstable effects. With the addition of a variety of postbiotics filtrates produced from fermented and metabolized probiotics, skin cells are enhanced in inhibiting lipid peroxidation and clearing free radicals, which greatly increases the antioxidant effect of the skin.

Many complex factors are contributing to the allergic redness of facial skin. Allergic skin irritation is divided into immediate and delayed types. Urticaria and drug rashes are classified as the immediate type, eczema and allergic dermatitis belong to the delayed type, and contact dermatitis refers to erythema, edema, and itching pains induced by the contact with a certain substance. In general, for most female patients, redness, edema, pain and itching accompanying the contact dermatitis are mostly induced by the improper use of cosmetics. Therefore, besides the conventional therapies using antihistamine and hormone drugs in hospitals, how to improve the allergic skin and restore the normal skin mechanism is a task that needs to be completed by a long-term skincare mechanism.

In terms of human factors, the long-term use of heavy metal cosmetics and the abuse of facial hormones lead to the retention of residual toxins on the skin epidermis, making skin susceptible to allergies and thinning the stratum corneum. As a result, allergies and erythema easily occur in an external environment with changeable temperatures. In addition, unhealthy living habits and heavy work pressure may also lead to metabolic disorders of the skin. These may also destroy the function of an original protective defense mechanism of the stratum corneum.

The urticaria with allergic redness may be induced by many pathogenic factors and shows the symptom of skin itching but without fever, nausea, vomiting, and asthma. In addition, allergens include fish, shrimp, crab, animal feathers, pollen, mushroom, nettle, drug, sunlight, bacteria, parasite, and the like. In daily life, people may touch a vast number of articles and eat a variety of food, and it is difficult to find out the cause of the disease for a while. They may feel a sharp itch and scratch it to break the erythema and blisters, which may cause infection. Consequently, some people suffer from recurrent urticaria with skin reddening.

BRIEF SUMMARY OF THE INVENTION

In view of the problems existing in the prior art, an object of the present invention is mainly to solve the technical problem and to provide a multi-postbiotics-compounded activating essence which has a good curative effect for people with recurrent allergic redness and can provide the energy required for restoring the original state of the skin, and a method for preparing the same.

To achieve the above object, the present invention provides the following technical solutions.

The present invention provides a multi-postbiotics-compounded rejuvenating essence, which includes the following components in percentage by weight: 8.0-13.0% of butanediol, 2.0-3.0% of triglyceride octoate/caprate/succinate, 2.0-3.0% of sodium pyrrolidone carboxylate, 2.0-3.0% of sodium polyglutamate, 1.0-2.0% of bio-saccharide gum-1, 1.0-1.5% of sodium hyaluronate, 0.5-1.0% of extract of Japanese *ardisia* herb stems, 0.5-1.0% of callus culture filtrate of *Crithmum maritimum,* 0.5-1.0% of yeast/rice ferment filtrate, 0.5-1.0% of fission yeast mycelium ferment filtrate, 0.5-1.0% of *lactobacillus*/mung bean extract/sodium glutamate ferment filtrate, 0.5-1.0% of *lactobacillus* ferment, 0.5-1.0% of *bacillus*/rice bran extract/soybean extract ferment filtrate, 0.5-1.0% of bifida ferment lysate, 0.5-1.0% of *Streptococcus thermophilus* ferment, 0.1-0.2% of collargol, and 65.3-79.4% of deionized water, wherein the essence is put in an airtight container and is injected with hydrogen gas.

Preferably, the multi-postbiotics-compounded rejuvenating essence includes the following components in percentage by weight: 10% of butanediol, 2.4% of triglyceride octoate/caprate/succinate, 2.6% of sodium pyrrolidone carboxylate, 2.5% of sodium polyglutamate, 1.3% of bio-saccharide gum-1, 1.2% of sodium hyaluronate, 0.9% of extract of Japanese *Ardisia* herb stems, 0.7% of callus culture filtrate of *Crithmum maritimum,* 0.6% of yeast/rice ferment filtrate, 0.8% of fission yeast mycelium ferment filtrate, 0.9% of *lactobacillus*/mung bean extract/sodium glutamate ferment filtrate, 0.7% of *lactobacillus* ferment, 0.6% of *bacillus*/rice bran extract/soybean extract ferment filtrate, 0.7% of bifida ferment lysate, 0.8% of *Streptococcus thermophilus* ferment, 0.1% of collargol, and 73.2% of deionized water, wherein the essence is put in an airtight container and is injected with hydrogen gas.

Preferably, the extract of Japanese *Ardisia* herb stems is prepared by pulverizing Japanese *Ardisia* herb stems by a pulverizer, performing supercritical extraction by taking denatured alcohol as a solvent in combination with carbon dioxide at properly adjusted temperature and pressure, and then releasing the pressure.

The triglyceride octoate/caprate/succinate is a lipid synthesized from medium-chain triglyceride and succinic acid and is featured with a specific gravity close to 1, which is close to that of water. It is capable of stabilizing emulsification and has a silky and non-sticky sense of touch and a good and special moisturizing property, which is conducive to reducing transepidermal water loss and brings good firmness and excellent film-forming property to the skin.

The sodium pyrrolidone carboxylate is a natural moisturizer derived from L-glutamic acid and is also one of the natural moisturizing factors present in the skin. It has excellent skin affinity and absorbability and is an excellent factor capable of moisturizing and replenishing water to the skin.

The sodium polyglutamate found in traditional natto is a viscous amino acid anionic polymer, which is also generally known as γ-polyglutamate. Such a polymer is an isomorphic polypeptide biopolymer with an amido bond formed by an α-amino and a β-carboxyl by taking polyglutamic acid as a structural unit. Due to the large number of hydrogen bonds formed by several hydrophilic groups, the natural moisturizing solid polyglutamate achieves strong water absorbability and moisturizing properties.

The bio-saccharide gum-1 per se is a polysaccharides substance, which is mainly prepared by a fermentation process taking corn and soybeans as a reaction substrate. Polysaccharide has a linear molecular structure, with a sequence consisting of three polysaccharide types, including L-fucose, D-galactose, and galacturonic acid. It has been demonstrated that a fucose component can participate in intercellular communication and cooperation, where intercellular communication refers to the exchange of biological signals between cells. Through the inter-cellular communication, skin cells such as keratinocyte, Langerhans' cells, and melanophores allow the skin to resist attacks to achieve a protective effect; and the fucose can achieve an effect of eliminating inflammation messengers, thereby relieving the skin from inflammation and pains and impeding the spread of allergic reactions.

The sodium hyaluronate prepared by fermenting natural *Bacillus subtilis* is greatly different from the common chemically synthesized sodium hyaluronate. Compared with the effect of the synthesized sodium hyaluronate, the refined sodium hyaluronate has been found to show superior water-retention capacity and time over the synthesized sodium hyaluronate. In particular, the time that a water-retention film resides on the stratum corneum of the skin is greatly increased.

In Traditional Chinese Medicine, Japanese *Ardisia* herb, also known as *Ardisia japonica*, mainly has the following curative effects: relieving cough, eliminating phlegm, detoxifying, and purifying blood. Active ingredients in the stems of Japanese *Ardisia* herb include bergenin No. 1 and bergenin No. 2. The total amount of bergenin is increased mainly by a supercritical extraction method.

*Crithmum maritimum* per se is a land organism derived from a beach plant. Stem cells of the *Crithmum maritimum* are extracted by a stem cell reaction generator and then lyophilized under low pressure. A filtrate prepared from these stem cells can be combined with skin cells to inhibit tyrosine enzymes in skin melanocytes, to activate the formation of endothelial cells and the proliferation of fibroblasts, and to promote the formation of collagen, thereby shortening the healing and repair time of a wound.

The *lactobacillus*/mung bean extract/sodium glutamate ferment filtrate shows a significant effect of reducing excessive inflammation and shortening the healing time for a skin wound. Its effect of inhibiting wound inflammation is equivalent to that of aspirin, an anti-inflammatory drug. In addition, it also has a significant effect on alleviating atopic dermatitis induced by an allergy.

As a metabolite of *bifidobacterium*, the bifida ferment lysate per se contains skin-care molecules including vitamin B complex, minerals, amino acids, and the like. It has a synergistic repair effect for skin irritation and cell DNA damage caused by ultraviolet radiation. In addition, the bifida ferment lysate shows a certain effect of clearing free radicals for the photoaging induced by the free radicals due to the ultraviolet radiation on the skin.

A method for preparing a multi-postbiotics-compounded rejuvenating essence comprises the following steps:
 (1) mixing butanediol, sodium pyrrolidone carboxylate, sodium polyglutamate, bio-saccharide gum-1, sodium hyaluronate, and deionized water, heating a resultant to 75-80° C., and stirring until complete dissolution to prepare a mixture;
 (2) pouring the mixture from Step (1) into a vacuum homogenizing emulsifier, starting stirring at a stirring speed of 500-700 rpm and a homogenizing speed of 1600-2000 rpm, vacuuming to 0.03-0.05 Mpa, and homogenizing and stirring for 3-10 min;
 (3) releasing a vacuum pressure, adding triglyceride octoate/caprate/succinate into the vacuum homogenizing emulsifier, starting stirring at a stirring speed of 500-700 rpm and a homogenizing speed of 1600-2000 rpm, vacuuming, and homogenizing and stirring for 2-5 min;
 (4) releasing the vacuum pressure, adding the extract of Japanese *Ardisia* herb stems, the callus culture filtrate of *Crithmum maritimum*, yeast/rice ferment filtrate, fission yeast mycelium ferment filtrate, *lactobacillus*/mung bean extract/sodium glutamate ferment filtrate, *lactobacillus* ferment, *bacillus*/rice bran extract/soybean extract ferment filtrate, bifida ferment lysate, *Streptococcus thermophilus* ferment, and collargol into the vacuum homogenizing emulsifier in sequence, and homogenizing and stirring for 5 min;
 (5) continuously stirring until the temperature is reduced to 35° C., discharging a resultant, screening the resultant by using an 80-120-mesh stainless steel strainer, and putting the results into a barrel for later use, thereby obtaining a semi-finished product of the essence; and
 (6) filling the semi-finished product into an airtight container, and injecting hydrogen into the semi-finished product at a controlled concentration of 0.5 ppm-5 ppm to prepare a packaged finished product.

The vacuum homogenizing emulsifier according to the present invention is a general-purpose device for producing medicinal ointment, high-grade cream, lotion, and the like, and can be purchased in the market. Its working principle is as follows: materials are stirred in the center of an upper section of an emulsification pot, in which a polytetrafluoroethylene scraper always fits a pot body to completely scrape the viscous materials sticking to a wall so that a new interface is constantly formed in the scraped materials; then the materials are cut, compressed, and folded by blades and rotating blades in such a way that they are stirred and mixed and flow down to a homogenizer below the pot body; the materials are then cut and rapidly pulverized into 200 nm-2 μm particles by processes such as strong cutting, impacting and turbulence created between a cutting wheel rotating at high speed and a fixed cutting sleeve; and the emulsification pot is in a vacuum state so that air bubbles generated during the process of stirring the materials are sucked away in time. Utilizing vacuolization, a produced item is not mixed the air bubbles during the stirring, so that it is ensured that a high-quality glossy and fine product with good extensibility is produced.

Preferably, the extract of Japanese *Ardisia* herb stems in Step (4) is prepared by pulverizing the Japanese *Ardisia* herb stems by a pulverizer, performing supercritical extraction by taking denatured alcohol as a solvent in combination with carbon dioxide at properly adjusted temperature and pressure, and then releasing the pressure.

Preferably, in Step (2), the stirring speed is 600 rpm, and the homogenizing speed is 1800 rpm.

Preferably, in Step (2), the vacuum homogenizing emulsifier is vacuumized to 0.04 Mpa.

Preferably, in Step (3), the stirring speed is 600 rpm, and the homogenizing speed is 1800 rpm.

Preferably, in Step (6), the concentration of the hydrogen injected into the airtight container is controlled at 3 ppm.

Compared with the prior art, the technical solutions according to the present invention have the following beneficial effects:

1. The extract of Japanese *Ardisia* herb stems in the present invention is conducive to reducing the probability of harmful bacterial staying on the skin and preventing the formation of Staphylococcus aureus and *Bacillus thuris* on the skin due to sebum secretion and abnormal living habits, and in addition, it has the effect of regulating the normal metabolism of skin cells to accelerate the repair of skin blotches;
2. The hydrogen is injected into the essence in the present invention to catalyze/activate various active substances in the essence for improving the activity of the components, which has a significant repair effect for the skin suffered from recurrent allergic redness; and
3. The essence according to the present invention contains a variety of active substances, which can enhance the general anti-oxidation and moisturizing effect of the skin to achieve the long-term skin-care effect of common skin-care products.

DETAILED DESCRIPTION OF THE INVENTION

The technical solutions in the embodiments of the present invention will be described clearly and completely below. The embodiments described are merely part of rather than all of the embodiments of the present invention. Based on the embodiments of the present invention, every other embodiment that can be achieved by a person of ordinary skills in the art without creative efforts shall fall within the protection scope of the present invention.

Embodiment 1

This embodiment relates to a multi-postbiotics-compounded rejuvenating essence, which includes the following components in percentage by weight: 10% of butanediol, 2.4% of triglyceride octoate/caprate/succinate, 2.6% of sodium pyrrolidone carboxylate, 2.5% of sodium polyglutamate, 1.3% of bio-saccharide gum-1, 1.2% of sodium hyaluronate, 0.9% of extract of Japanese *Ardisia* herb stems, 0.7% of callus culture filtrate of *Crithmum maritimum*, 0.6% of yeast/rice ferment filtrate, 0.8% of fission yeast mycelium ferment filtrate, 0.9% of *lactobacillus*/mung bean extract/sodium glutamate ferment filtrate, 0.7% of *lactobacillus* ferment, 0.6% of *bacillus*/rice bran extract/soybean extract ferment filtrate, 0.7% of bifida ferment lysate, 0.8% of *Streptococcus thermophilus* ferment, 0.1% of collargol, and 73.2% of deionized water, wherein the essence is put in an airtight container and is injected with hydrogen.

The essence described above was prepared by the following steps:
(1) butanediol, sodium pyrrolidone carboxylate, sodium polyglutamate, bio-saccharide gum-1, sodium hyaluronate, and deionized water were mixed, heated to 75° C., and stirred until complete dissolution to prepare a mixture;
(2) the mixture prepared in Step (1) was poured into a vacuum homogenizing emulsifier, which was vacuumized to 0.04 Mpa, and the mixture was homogenized and stirred by stirring blades for 10 min at a stirring speed of 600 rpm and a homogenizing speed of 1800 rpm;
(3) a vacuum pressure was released, triglyceride octoate/caprate/succinate were added into the vacuum homogenizing emulsifier, and homogenizing and stirring were started and lasted for 3 min at a stirring speed of 600 rpm and a homogenizing speed of 1800 rpm;
(4) the vacuum pressure was released, and the extract of Japanese *Ardisia* herb stems, the callus culture filtrate of *Crithmum maritimum*, yeast/rice ferment filtrate, fission yeast mycelium ferment filtrate, *lactobacillus*/mung bean extract/sodium glutamate ferment filtrate, *lactobacillus* ferment, *bacillus*/rice bran extract/soybean extract ferment filtrate, bifida ferment lysate, *Streptococcus thermophilus* ferment, and collargol were added into the vacuum homogenizing emulsifier in sequence, and homogenized and stirred for 5 min;
(5) the mixture was continuously stirred until the temperature was reduced to 35° C. and then discharged, and the mixture was screened by using a 100-mesh stainless steel strainer, and put into a barrel for later use, thereby obtaining a semi-finished product of the essence; and
(6) the semi-finished product was filled into an airtight container, and hydrogen was injected into the semi-finished product to prepare a finished product.

The extract of Japanese *Ardisia* herb stems in Step (4) was prepared by pulverizing the Japanese *Ardisia* herb stems by a pulverizer, performing supercritical extraction by taking denatured alcohol as a solvent in combination with carbon dioxide at properly adjusted temperature and pressure, and then releasing the pressure.

In Step (6), the concentration of the hydrogen injected into the airtight container was controlled at 3 ppm.

Embodiment 2

This embodiment relates to a multi-postbiotics-compounded rejuvenating essence, which includes the following components in percentage by weight: 8.0% of butanediol, 2.0% of triglyceride octoate/caprate/succinate, 2.0% of sodium pyrrolidone carboxylate, 2.0% of sodium polyglutamate, 1.0% of bio-saccharide gum-1, 1.0% of sodium hyaluronate, 0.5% of extract of Japanese *ardisia* herb stems, 0.50% of callus culture filtrate of *Crithmum maritimum*, 0.5% of yeast/rice ferment filtrate, 0.5% of fission yeast mycelium ferment filtrate, 0.5% of *lactobacillus*/mung bean extract/sodium glutamate ferment filtrate, 0.5% of *lactobacillus* ferment, 0.5% of *bacillus*/rice bran extract/soybean extract ferment filtrate, 0.5% of bifida ferment lysate, 0.5% of *Streptococcus thermophilus* ferment, 0.1% of collargol, and 79.4% of deionized water, wherein the essence is put in an airtight container and is injected with hydrogen.

The essence described above was prepared by the following steps:
(1) butanediol, sodium pyrrolidone carboxylate, sodium polyglutamate, bio-saccharide gum-1, sodium hyaluronate, and deionized water were mixed, heated to 75° C., and stirred until complete dissolution to prepare a mixture;
(2) the mixture prepared in Step (1) was poured into a vacuum homogenizing emulsifier, which was vacuumized to 0.04 Mpa, and the mixture was homogenized and stirred by stirring blades for 10 min at a stirring speed of 600 rpm and a homogenizing speed of 1800 rpm;
(3) a vacuum pressure was released, triglyceride octoate/caprate/succinate were added into the vacuum homogenizing emulsifier, and homogenizing and stirring were started and lasted for 3 min at a stirring speed of 600 rpm and a homogenizing speed of 1800 rpm;
(4) the vacuum pressure was released, and the extract of Japanese *Ardisia* herb stems, the callus culture filtrate of *Crithmum maritimum*, yeast/rice ferment filtrate, fission yeast mycelium ferment filtrate, *lactobacillus*/mung bean extract/sodium glutamate ferment filtrate, *lactobacillus* ferment, *bacillus*/rice bran extract/soybean extract ferment filtrate, bifida ferment lysate, *Streptococcus thermophilus* ferment, and collargol were added into the vacuum homogenizing emulsifier in sequence, and homogenized and stirred for 5 min;
(5) the mixture was continuously stirred until the temperature was reduced to 35° C. and then discharged, and the mixture was screened by using a 100-mesh stainless steel strainer, and put into a barrel for later use, thereby obtaining a semi-finished product of the essence; and
(6) the semi-finished product was filled into an airtight container, and hydrogen was injected into the semi-finished product to prepare a finished product.

The extract of Japanese *Ardisia* herb stems in Step (4) was prepared by pulverizing the Japanese *Ardisia* herb stems by a pulverizer, performing supercritical extraction by taking denatured alcohol as a solvent in combination with carbon dioxide at properly adjusted temperature and pressure, and then releasing the pressure.

In Step (6), the concentration of the hydrogen injected into the airtight container was controlled at 1 ppm.

Embodiment 3

This embodiment relates to a multi-postbiotics-compounded rejuvenating essence, which includes the following components in percentage by weight: 8.0% of butanediol, 2.0% of triglyceride octoate/caprate/succinate, 2.0% of sodium pyrrolidone carboxylate, 2.0% of sodium polyglutamate, 1.0% of bio-saccharide gum-1, 1.0% of sodium hyaluronate, 0.5% of extract of Japanese *ardisia* herb stems, 0.5% of callus culture filtrate of *Crithmum maritimum*, 0.5% of yeast/rice ferment filtrate, 0.5% of fission yeast mycelium ferment filtrate, 0.5% of *lactobacillus*/mung bean extract/sodium glutamate ferment filtrate, 0.5% of *lactobacillus* ferment, 0.5% of *bacillus*/rice bran extract/soybean extract ferment filtrate, 0.5% of bifida ferment lysate, 0.5% of *Streptococcus thermophilus* ferment, 0.1% of collargol, and 79.4% of deionized water, wherein the essence is put in an airtight container and is injected with hydrogen.

The essence described above was prepared by the following steps:
(1) butanediol, sodium pyrrolidone carboxylate, sodium polyglutamate, bio-saccharide gum-1, sodium hyaluronate, and deionized water were mixed, heated to 75° C., and stirred until complete dissolution to prepare a mixture;
(2) the mixture prepared in Step (1) was poured into a vacuum homogenizing emulsifier, which was vacuumized to 0.04 Mpa, and the mixture was homogenized and stirred by stirring blades for 10 min at a stirring speed of 600 rpm and a homogenizing speed of 1800 rpm;
(3) a vacuum pressure was released, triglyceride octoate/caprate/succinate were added into the vacuum homogenizing emulsifier, and homogenizing and stirring were started and lasted for 3 min at a stirring speed of 600 rpm and a homogenizing speed of 1800 rpm;
(4) the vacuum pressure was released, and the extract of Japanese *Ardisia* herb stems, the callus culture filtrate of *Crithmum maritimum*, yeast/rice ferment filtrate, fission yeast mycelium ferment filtrate, *lactobacillus*/mung bean extract/sodium glutamate ferment filtrate, *lactobacillus* ferment, *bacillus*/rice bran extract/soybean extract ferment filtrate, bifida ferment lysate, *Streptococcus thermophilus* ferment, and collargol were added into the vacuum homogenizing emulsifier in sequence, and homogenized and stirred for 5 min;
(5) the mixture was continuously stirred until the temperature was reduced to 35° C. and then discharged, and the mixture was screened by using a 100-mesh stainless steel strainer, and put into a barrel for later use, thereby obtaining a semi-finished product of the essence; and
(6) the semi-finished product was filled into an airtight container, and hydrogen was injected into the semi-finished product to prepare a finished product.

The extract of Japanese *Ardisia* herb stems in Step (4) was prepared by pulverizing the Japanese *Ardisia* herb stems by a pulverizer, performing supercritical extraction by taking denatured alcohol as a solvent in combination with carbon dioxide at properly adjusted temperature and pressure, and then releasing the pressure.

In Step (6), the concentration of the hydrogen injected into the airtight container was controlled at 3 ppm.

Embodiment 4

This embodiment relates to a multi-postbiotics-compounded rejuvenating essence, which includes the following components in percentage by weight: 9.0% of butanediol, 2.0% of triglyceride octoate/caprate/succinate, 3.0% of sodium pyrrolidone carboxylate, 2.0% of sodium polyglutamate, 2.0% of bio-saccharide gum-1, 1.0% of sodium hyaluronate, 1.0% of extract of Japanese *Ardisia* herb stems, 0.5% of callus culture filtrate of *Crithmum maritimum*, 0.5% of yeast/rice ferment filtrate, 1.0% of fission yeast mycelium ferment filtrate, 0.5% of *lactobacillus*/mung bean extract/sodium glutamate ferment filtrate, 0.5% of *lactobacillus* ferment, 1.0% of *bacillus*/rice bran extract/soybean extract ferment filtrate, 0.5% of bifida ferment lysate, 1.0% of *Streptococcus thermophilus* ferment, 0.1% of collargol, and 74.4% of deionized water, wherein the essence is put in an airtight container and is injected with hydrogen.

The essence described above was prepared by the following steps:
(1) butanediol, sodium pyrrolidone carboxylate, sodium polyglutamate, bio-saccharide gum-1, sodium hyaluronate, and deionized water were mixed, heated to 75° C., and stirred until complete dissolution to prepare a mixture;
(2) the mixture prepared in Step (1) was poured into a vacuum homogenizing emulsifier, which was vacuumized to 0.04 Mpa, and the mixture was homogenized and stirred by stirring blades for 10 min at a stirring speed of 600 rpm and a homogenizing speed of 1800 rpm;
(3) a vacuum pressure was released, triglyceride octoate/caprate/succinate were added into the vacuum homogenizing emulsifier, and homogenizing and stirring were started and lasted for 3 min at a stirring speed of 600 rpm and a homogenizing speed of 1800 rpm;
(4) the vacuum pressure was released, and the extract of Japanese *Ardisia* herb stems, the callus culture filtrate of *Crithmum maritimum*, yeast/rice ferment filtrate, fission yeast mycelium ferment filtrate, *lactobacillus*/mung bean extract/sodium glutamate ferment filtrate, *lactobacillus* ferment, *bacillus*/rice bran extract/soybean extract ferment filtrate, bifida ferment lysate, *Streptococcus thermophilus* ferment, and collargol were added into the vacuum homogenizing emulsifier in sequence, and homogenized and stirred for 5 min;
(5) the mixture was continuously stirred until the temperature was reduced to 35° C. and then discharged, and the mixture was screened by using a 100-mesh stainless steel strainer, and put into a barrel for later use, thereby obtaining a semi-finished product of the essence; and
(6) the semi-finished product was filled into an airtight container, and hydrogen was injected into the semi-finished product to prepare a finished product.

The extract of Japanese *Ardisia* herb stems in Step (4) was prepared by pulverizing the Japanese *Ardisia* herb stems by a pulverizer, performing supercritical extraction by taking denatured alcohol as a solvent in combination with carbon dioxide at properly adjusted temperature and pressure, and then releasing the pressure.

In Step (6), the concentration of the hydrogen injected into the airtight container was controlled at 3 ppm.

Embodiment 5

This embodiment relates to a multi-postbiotics-compounded rejuvenating essence, which includes the following components in percentage by weight: 13.0% of butanediol, 2.5% of triglyceride octoate/caprate/succinate, 2.5% of sodium pyrrolidone carboxylate, 3.0% of sodium polyglutamate, 1.0% of bio-saccharide gum-1, 1.2% of sodium hyaluronate, 0.6% of extract of Japanese *Ardisia* herb stems, 0.5% of callus culture filtrate of *Crithmum maritimum*, 1.0% of yeast/rice ferment filtrate, 0.6% of fission yeast mycelium ferment filtrate, 0.7% of *lactobacillus*/mung bean extract/sodium glutamate ferment filtrate, 0.5% of *lactobacillus* ferment, 0.8% of *bacillus*/rice bran extract/soybean extract ferment filtrate, 0.7% of bifida ferment lysate, 1.0% of *Streptococcus thermophilus* ferment, 0.2% of collargol, and 71.2% of deionized water, wherein the essence is put in an airtight container and is injected with hydrogen.

The essence described above was prepared by the following steps:
(1) butanediol, sodium pyrrolidone carboxylate, sodium polyglutamate, bio-saccharide gum-1, sodium hyaluronate, and deionized water were mixed, heated to 75° C., and stirred until complete dissolution to prepare a mixture;
(2) the mixture prepared in Step (1) was poured into a vacuum homogenizing emulsifier, which was vacuumized to 0.04 Mpa, and the mixture was homogenized and stirred by stirring blades for 10 min at a stirring speed of 600 rpm and a homogenizing speed of 1800 rpm;
(3) a vacuum pressure was released, triglyceride octoate/caprate/succinate were added into the vacuum homogenizing emulsifier, and homogenizing and stirring were started and lasted for 3 min at a stirring speed of 600 rpm and a homogenizing speed of 1800 rpm;
(4) the vacuum pressure was released, and the extract of Japanese *Ardisia* herb stems, the callus culture filtrate of *Crithmum maritimum*, yeast/rice ferment filtrate, fission yeast mycelium ferment filtrate, *lactobacillus*/mung bean extract/sodium glutamate ferment filtrate, *lactobacillus* ferment, *bacillus*/rice bran extract/soybean extract ferment filtrate, bifida ferment lysate, *Streptococcus thermophilus* ferment, and collargol were added into the vacuum homogenizing emulsifier in sequence, and homogenized and stirred for 5 min;
(5) the mixture was continuously stirred until the temperature was reduced to 35° C. and then discharged, and the mixture was screened by using a 100-mesh stainless steel strainer, and put into a barrel for later use, thereby obtaining a semi-finished product of the essence; and
(6) the semi-finished product was filled into an airtight container, and hydrogen was injected into the semi-finished product to prepare a finished product.

The extract of Japanese *Ardisia* herb stems in Step (4) was prepared by pulverizing the Japanese *Ardisia* herb stems by a pulverizer, performing supercritical extraction by taking denatured alcohol as a solvent in combination with carbon dioxide at properly adjusted temperature and pressure, and then releasing the pressure.

In Step (6), the concentration of the hydrogen injected into the airtight container is controlled at 3 ppm.

Embodiment 6

This embodiment relates to a multi-postbiotics-compounded rejuvenating essence, which includes the following components in percentage by weight: 12.0% of butanediol, 2.5% of triglyceride octoate/caprate/succinate, 3% of sodium pyrrolidone carboxylate, 2.5% of sodium polyglutamate, 1.2% of bio-saccharide gum-1, 1.5% of sodium hyaluronate, 1.0% of extract of Japanese *Ardisia* herb stems, 1.0% of callus culture filtrate of *Crithmum maritimum*, 0.6% of yeast/rice ferment filtrate, 0.5% of fission yeast mycelium ferment filtrate, 0.9% of *lactobacillus*/mung bean extract/sodium glutamate ferment filtrate, 0.9% of *lactobacillus* ferment, 0.5% of *bacillus*/rice bran extract/soybean extract ferment filtrate, 0.6% of bifida ferment lysate, 1.0% of *Streptococcus thermophilus* ferment, 0.2% of collargol, and 70.1% of deionized water, wherein the essence is put in an airtight container and is injected with hydrogen.

The essence described above was prepared by the following steps:
(1) butanediol, sodium pyrrolidone carboxylate, sodium polyglutamate, bio-saccharide gum-1, sodium hyaluronate, and deionized water were mixed, heated to 75° C., and stirred until complete dissolution to prepare a mixture;
(2) the mixture prepared in Step (1) was poured into a vacuum homogenizing emulsifier, which was vacuumized to 0.04 Mpa, and the mixture was homogenized and stirred by stirring blades for 10 min at a stirring speed of 600 rpm and a homogenizing speed of 1800 rpm;
(3) a vacuum pressure was released, triglyceride octoate/caprate/succinate were added into the vacuum homogenizing emulsifier, and homogenizing and stirring were started and lasted for 3 min at a stirring speed of 600 rpm and a homogenizing speed of 1800 rpm;
(4) the vacuum pressure was released, and the extract of Japanese *Ardisia* herb stems, the callus culture filtrate of *Crithmum maritimum*, yeast/rice ferment filtrate, fission yeast mycelium ferment filtrate, *lactobacillus*/mung bean extract/sodium glutamate ferment filtrate, *lactobacillus* ferment, *bacillus*/rice bran extract/soybean extract ferment filtrate, bifida ferment lysate, *Streptococcus thermophilus* ferment, and collargol were added into the vacuum homogenizing emulsifier in sequence, and homogenized and stirred for 5 min;

(5) the mixture was continuously stirred until the temperature was reduced to 35° C. and then discharged, and the mixture was screened by using a 100-mesh stainless steel strainer, and put into a barrel for later use, thereby obtaining a semi-finished product of the essence; and (6) the semi-finished product was filled into an airtight container, and hydrogen was injected into the semi-finished product to prepare a finished product.

The extract of Japanese *Ardisia* herb stems in Step (4) was prepared by pulverizing the Japanese *Ardisia* herb stems by a pulverizer, performing supercritical extraction by taking denatured alcohol as a solvent in combination with carbon dioxide at properly adjusted temperature and pressure, and then releasing the pressure.

In Step (6), the intensity of pressure in the airtight container is 2 Mpa after the hydrogen is injected.

Comparative Example 1

This comparative example relates to a multi-postbiotics-compounded rejuvenating essence, which includes the following components in percentage by weight: 10% of butanediol, 2.4% of triglyceride octoate/caprate/succinate, 2.6% of sodium pyrrolidone carboxylate, 2.5% of sodium polyglutamate, 1.3% of bio-saccharide gum-1, 1.2% of sodium hyaluronate, 0.9% of extract of Japanese *ardisia* herb stems, 0.7% of callus culture filtrate of *Crithmum maritimum*, 0.6% of yeast/rice ferment filtrate, 0.8% of fission yeast mycelium ferment filtrate, 0.9% of *lactobacillus*/mung bean extract/sodium glutamate ferment filtrate, 0.7% of *lactobacillus* ferment, 0.6% of *bacillus*/rice bran extract/soybean extract ferment filtrate, 0.7% of bifida ferment lysate, 0.8% of *Streptococcus thermophilus* ferment, 0.1% of collargol, and 73.2% of deionized water.

The essence described above was prepared by the following steps:

(1) butanediol, sodium pyrrolidone carboxylate, sodium polyglutamate, bio-saccharide gum-1, sodium hyaluronate, and deionized water were mixed, heated to 75° C., and stirred until complete dissolution to prepare a mixture;

(2) the mixture prepared in Step (1) was poured into a vacuum homogenizing emulsifier, which was vacuumized to 0.04 Mpa, and the mixture was homogenized and stirred by stirring blades for 10 min at a stirring speed of 600 rpm and a homogenizing speed of 1800 rpm;

(3) a vacuum pressure was released, triglyceride octoate/caprate/succinate was added into the vacuum homogenizing emulsifier, and homogenizing and stirring were started and lasted for 3 min at a stirring speed of 600 rpm and a homogenizing speed of 1800 rpm;

(4) the vacuum pressure was released, and the extract of Japanese *Ardisia* herb stems, the callus culture filtrate of *Crithmum maritimum*, yeast/rice ferment filtrate, fission yeast mycelium ferment filtrate, *lactobacillus*/mung bean extract/sodium glutamate ferment filtrate, *lactobacillus* ferment, *bacillus*/rice bran extract/soybean extract ferment filtrate, bifida ferment lysate, *Streptococcus thermophilus* ferment, and collargol were added into the vacuum homogenizing emulsifier in sequence, and homogenized and stirred for 5 min; and (5) the mixture was continuously stirred until the temperature was reduced to 35° C. and then discharged, and the mixture was screened by using a 100-mesh stainless steel strainer, and put into a barrel for later use, thereby obtaining a finished product.

The extract of Japanese *Ardisia* herb stems in Step (4) was prepared by pulverizing the Japanese *ardisia* herb stems by a pulverizer, performing supercritical extraction by taking denatured alcohol as a solvent in combination with carbon dioxide at properly adjusted temperature and pressure, and then releasing the pressure.

Comparative Example 2

This comparative example relates to a multi-postbiotics-compounded rejuvenating essence, which includes the following components in percentage by weight: 10% of butanediol, 2.4% of triglyceride octoate/caprate/succinate, 2.6% of sodium pyrrolidone carboxylate, 2.5% of sodium polyglutamate, 1.3% of bio-saccharide gum-1, 1.2% of sodium hyaluronate, 0.7% of callus culture filtrate of *Crithmum maritimum*, 0.6% of yeast/rice ferment filtrate, 0.8% of fission yeast mycelium ferment filtrate, 0.9% of *lactobacillus*/mung bean extract/sodium glutamate ferment filtrate, 0.7% of *lactobacillus* ferment, 0.6% of *bacillus*/rice bran extract/soybean extract ferment filtrate, 0.7% of bifida ferment lysate, 0.8% of *Streptococcus thermophilus* ferment, 0.1% of collargol, and 73.2% of deionized water, wherein the essence is put in an airtight container and is injected with hydrogen gas.

The essence described above was prepared by the following steps:

(1) butanediol, sodium pyrrolidone carboxylate, sodium polyglutamate, bio-saccharide gum-1, sodium hyaluronate, and deionized water were mixed, heated to 75° C., and stirred until complete dissolution to prepare a mixture;

(2) the mixture prepared in Step (1) was poured into a vacuum homogenizing emulsifier, which was vacuumized to 0.04 Mpa, and the mixture was homogenized and stirred by stirring blades for 10 min at a stirring speed of 600 rpm and a homogenizing speed of 1800 rpm;

(3) a vacuum pressure was released, triglyceride octoate/caprate/succinate were added into the vacuum homogenizing emulsifier, and homogenizing and stirring were started and lasted for 3 min at a stirring speed of 600 rpm and a homogenizing speed of 1800 rpm;

(4) the emulsifier was vacummized, the mixture was stirred and cooled to 45° C., and the extract of Japanese *Ardisia* herb stems, the callus culture filtrate of *Crithmum maritimum*, yeast/rice ferment filtrate, fission yeast mycelium ferment filtrate, *lactobacillus*/mung bean extract/sodium glutamate ferment filtrate, *lactobacillus* ferment, *bacillus*/rice bran extract/soybean extract ferment filtrate, bifida ferment lysate, *Streptococcus thermophilus* ferment, and collargol were added into the vacuum homogenizing emulsifier in sequence, and homogenized and stirred for 5 min; and (5) the mixture was continuously stirred until the temperature was reduced to 35° C. and then discharged, and the mixture was screened by using a 100-mesh stainless steel strainer, and put into a barrel for later use, thereby obtaining a semi-finished product of the essence; and (6) the semi-finished product was filled into an airtight container, and hydrogen was injected into the semi-finished product to prepare a finished product. The concentration of the hydrogen injected into the airtight container was controlled at 3 ppm.

Comparative Example 3

This comparative example relates to a multi-postbiotics-compounded rejuvenating essence, which includes the following components in percentage by weight: 10% of butanediol, 2.4% of triglyceride octoate/caprate/succinate, 2.6% of sodium pyrrolidone carboxylate, 2.5% of sodium polyglutamate, 1.3% of bio-saccharide gum-1, 1.2% of sodium hyaluronate, 0.7% of callus culture filtrate of *Crithmum maritimum*, 0.6% of yeast/rice ferment filtrate, 0.8% of fission yeast mycelium ferment filtrate, 0.9% of *lactobacillus*/mung bean extract/sodium glutamate ferment filtrate, 0.7% of *lactobacillus* ferment, 0.6% of *bacillus*/rice bran extract/soybean extract ferment filtrate, 0.7% of bifida ferment lysate, 0.8% of *Streptococcus thermophilus* ferment, 0.1% of collargol, and 73.2% of deionized water.

The essence described above was prepared by the following steps:

(1) butanediol, sodium pyrrolidone carboxylate, sodium polyglutamate, bio-saccharide gum-1, sodium hyaluronate, and deionized water were mixed, heated to 75° C., and stirred until complete dissolution to prepare a mixture;

(2) the mixture prepared in Step (1) was poured into a vacuum homogenizing emulsifier, which was vacuumized to 0.04 Mpa, and the mixture was homogenized and stirred by stirring blades for 10 min at a stirring speed of 600 rpm and a homogenizing speed of 1800 rpm;

(3) a vacuum pressure was released, triglyceride octoate/caprate/succinate were added into the vacuum homogenizing emulsifier, and homogenizing and stirring were started and lasted for 3 min at a stirring speed of 600 rpm and a homogenizing speed of 1800 rpm;

(4) the emulsifier was vacummized, the mixture was stirred and cooled to 45° C., and the extract of Japanese *Ardisia* herb stems, the callus culture filtrate of *Crithmum maritimum*, yeast/rice ferment filtrate, fission yeast mycelium ferment filtrate, *lactobacillus*/mung bean extract/sodium glutamate ferment filtrate, *lactobacillus* ferment, *bacillus*/rice bran extract/soybean extract ferment filtrate, bifida ferment lysate, *Streptococcus thermophilus* ferment, and collargol were added into the vacuum homogenizing emulsifier in sequence, and homogenized and stirred for 5 min; and (5) the mixture was continuously stirred until the temperature was reduced to 35° C. and then discharged, and the mixture was screened by using a 100-mesh stainless steel strainer, and put into a barrel for later use, thereby obtaining a finished product.

Effect Embodiment

The essence was packaged in an airtight container. When in use, the airtight container needed to be sealed immediately after the essence is squeezed out. To understand the effect of the present invention in practical use, the essences were prepared based on the component ratios in Embodiments 1 to 6 and in Comparative Examples 1 to 3. A wide investigation was conducted on a trial basis utilizing a questionnaire survey. This survey included 2700 male and female trial users with the symptoms of recurring allergic redness and rashes, with 300 trial users in each group. There were 1478 male users and 1222 female users, with the age ranging from 16 to 55 and the average age of about 40. A total of 2156 valid questionnaires were retrieved.

The skin-care effects of the essences from the Comparative Examples 1 to 3 and from the Embodiments 1 to 6 as described above are shown in Table 1.

TABLE 1

| | Proportion of trial users with alleviated skin dullness | Proportion of trial users with improved skin moisturization | Proportion of trial users with reduced allergic erythema | Proportion of trial users with eliminated skin rashes | Proportion of trial users with reduced recurrent allergic redness and rashes |
|---|---|---|---|---|---|
| Comparative Example 1 | 56.83% | 53.23% | 36.52% | 79.67% | 30.25% |
| Comparative Example 2 | 57.89% | 56.30% | 52.44% | 56.83% | 55.21% |
| Comparative Example 3 | 56.83% | 56.83% | 11.34% | 31.32% | 10.31% |
| Embodiment 1 | 93.26% | 94.67% | 96.86% | 96.42% | 97.23% |
| Embodiment 2 | 86.74% | 83.27% | 89.11% | 88.25% | 86.13% |
| Embodiment 3 | 87.32% | 85.65% | 90.13% | 90.21% | 87.96% |
| Embodiment 4 | 89.55% | 92.01% | 92.53% | 92.36% | 90.11% |
| Embodiment 5 | 90.01% | 91.55% | 94.74% | 91.38% | 92.61% |
| Embodiment 6 | 89.55% | 90.36% | 93.23% | 92.71% | 90.62% |

In summary, the present invention shows significant effects on alleviating skin dullness, improving skin moisturization, reducing the amount of allergic erythema, eliminating the number of skin rashes, and reducing the recurrent allergic redness and rashes to a different extent, and can achieve a good effect of curing the recurrent allergic redness and rashes for consumers.

The extract of Japanese *Ardisia* herb stems shows a significant effect on eliminating the skin erythema and can achieve an effect of repairing the skin. After the hydrogen is injected into the essence, the combination of active substances has a prominent effect on reducing the amount of allergic erythema and alleviating the recurrent allergic redness and rashes.

The skin-care effect achieved based on the component ratios in Embodiment 1 is the best.

Described above are merely embodiments of the present invention, and are not intended to limit the patent scope of the present invention. Any equivalent structures or equivalent flow transformations based on the specification of the present invention, or any direct or indirect applications to other relevant technical fields, shall be likewise construed as falling within the patent scope of the present invention.

What is claimed is:

1. A multi-postbiotics-compounded rejuvenating essence, comprising the following components in percentage by weight: 8.0-13.0% of butanediol, 2.0-3.0% of triglyceride octoate/caprate/succinate, 2.0-3.0% of sodium pyrrolidone carboxylate, 2.0-3.0% of sodium polyglutamate, 1.0-2.0% of bio-saccharide gum-1, 1.0-1.5% of sodium hyaluronate, 0.5-1.0% of extract of Japanese *ardisia* herb stems, 0.5-1.0% of callus culture filtrate of *Crithmum maritimum,* 0.5-1.0% of yeast/rice ferment filtrate, 0.5-1.0% of fission yeast mycelium ferment filtrate, 0.5-1.0% of *lactobacillus*/mung bean extract/sodium glutamate ferment filtrate, 0.5-1.0% of *lactobacillus* ferment, 0.5-1.0% of *bacillus*/rice bran extract/soybean extract ferment filtrate, 0.5-1.0% of bifida ferment lysate, 0.5-1.0% of *Streptococcus thermophilus* ferment, 0.1-0.2% of collargol, and 65.3-79.4% of deionized water, wherein the essence is put in an airtight container and is injected with hydrogen.

2. The multi-postbiotics-compounded rejuvenating essence according to claim 1, comprising the following components in percentage by weight: 10% of butanediol, 2.4% of triglyceride octoate/caprate/succinate, 2.6% of sodium pyrrolidone carboxylate, 2.5% of sodium polyglutamate, 1.3% of bio-saccharide gum-1, 1.2% of sodium hyaluronate, 0.9% of extract of Japanese *Ardisia* herb stems, 0.7% of callus culture filtrate of *Crithmum maritimum,* 0.6% of yeast/rice ferment filtrate, 0.8% of fission yeast mycelium ferment filtrate, 0.9% of *lactobacillus*/mung bean extract/sodium glutamate ferment filtrate, 0.7% of *lactobacillus* ferment, 0.6% of *bacillus*/rice bran extract/soybean extract ferment filtrate, 0.7% of bifida ferment lysate, 0.8% of *Streptococcus thermophilus* ferment, 0.1% of collargol, and 73.2% of deionized water, wherein the essence is put in the airtight container and is injected with hydrogen.

3. The multi-postbiotics-compounded rejuvenating essence according to claim 1, wherein the extract of Japanese *Ardisia* herb stems is prepared by pulverizing Japanese *Ardisia* herb stems by a pulverizer, performing supercritical extraction by taking denatured alcohol as a solvent in combination with carbon dioxide at properly adjusted temperature and pressure, and then releasing the pressure.

4. A method for preparing the multi-postbiotics-compounded rejuvenating essence according to claim 1, comprising the following steps:
   (1) mixing the butanediol, the sodium pyrrolidone carboxylate, the sodium polyglutamate, the bio-saccharide gum-1, the sodium hyaluronate, and the deionized water, heating a resultant to 75-80° C., and stirring until complete dissolution to prepare a mixture;
   (2) pouring the mixture from Step (1) into a vacuum homogenizing emulsifier, starting stirring at a stirring speed of 500-700 rpm and a homogenizing speed of 1600-2000 rpm, vacuuming to 0.03-0.05 Mpa, and homogenizing and stirring for 3-10 min;
   (3) releasing vacuum pressure, adding the triglyceride octoate/caprate/succinate into the vacuum homogenizing emulsifier, starting stirring at a stirring speed of 500-700 rpm and a homogenizing speed of 1600-2000 rpm, vacuuming, and homogenizing and stirring for 2-5 min;
   (4) releasing the vacuum pressure, adding the extract of Japanese *Ardisia* herb stems, the callus culture filtrate of *Crithmum maritimum*, the yeast/rice ferment filtrate, the fission yeast mycelium ferment filtrate, the *lactobacillus*/mung bean extract/sodium glutamate ferment filtrate, the *lactobacillus* ferment, *bacillus*/rice bran extract/soybean extract ferment filtrate, the bifida ferment lysate, the *Streptococcus thermophilus* ferment, and the collargol into the vacuum homogenizing emulsifier in sequence, and homogenizing and stirring for 5 min;
   (5) continuously stirring until the temperature is reduced to 35° C., discharging a resultant, screening the resultant by using an 80-120-mesh stainless steel strainer, and putting the results into a barrel for later use, thereby obtaining a semi-finished product of the essence; and
   (6) filling the semi-finished product into an airtight container, and injecting hydrogen into the semi-finished product at a controlled concentration of 0.5 ppm-5 ppm to prepare a packaged finished product.

5. The method for preparing the multi-postbiotics-compounded rejuvenating essence according to claim 4, wherein the extract of Japanese *Ardisia* herb stems in Step (4) is prepared by pulverizing the Japanese *Ardisia* herb stems by a pulverizer, performing supercritical extraction by taking denatured alcohol as a solvent in combination with carbon dioxide at properly adjusted temperature and pressure, and then releasing the pressure.

6. The method for preparing the multi-postbiotics-compounded rejuvenating essence according to claim 4, wherein in Step (2), the stirring speed is 600 rpm, and the homogenizing speed is 1800 rpm.

7. The method for preparing the multi-postbiotics-compounded rejuvenating essence according to claim 4, wherein in Step (2), the vacuum homogenizing emulsifier is vacuumized to 0.04 Mpa.

8. The method for preparing the multi-postbiotics-compounded rejuvenating essence according to claim 4, wherein in Step (3), the stirring speed is 600 rpm, and the homogenizing speed is 1800 rpm.

9. The method for preparing the multi-postbiotics-compounded rejuvenating essence according to claim 4, wherein in Step (6), the concentration of the hydrogen injected into the airtight container is controlled at 3 ppm.

* * * * *